(12) United States Patent
Koseoglu et al.

(10) Patent No.: US 10,844,295 B1
(45) Date of Patent: Nov. 24, 2020

(54) SYSTEMS AND PROCESSES TO DEOLEFINATE AROMATIC-RICH HYDROCARBON STREAMS

(71) Applicant: Saudi Arabian Oil Company, Dhahran (SA)

(72) Inventors: Omer Refa Koseoglu, Dhahran (SA); Robert Peter Hodgkins, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/600,055

(22) Filed: Oct. 11, 2019

(51) Int. Cl.
| | |
|---|---|
| C10G 53/00 | (2006.01) |
| C07C 29/04 | (2006.01) |
| B01J 8/00 | (2006.01) |
| C10L 10/00 | (2006.01) |
| C10G 53/14 | (2006.01) |
| C10L 1/182 | (2006.01) |
| C10L 10/10 | (2006.01) |
| B01J 8/02 | (2006.01) |

(52) U.S. Cl.
CPC ............ C10G 53/14 (2013.01); B01J 8/0278 (2013.01); C07C 29/04 (2013.01); C10L 1/1822 (2013.01); C10L 10/10 (2013.01); C10G 2300/1044 (2013.01); C10G 2300/1088 (2013.01); C10G 2300/201 (2013.01); C10G 2300/301 (2013.01); C10G 2400/30 (2013.01); C10L 2200/0423 (2013.01); C10L 2270/023 (2013.01); C10L 2290/543 (2013.01)

(58) Field of Classification Search
CPC ......... C10G 53/14; C07C 29/04; C10L 10/10; B01J 8/0278
See application file for complete search history.

(56) References Cited

U.S. PATENT DOCUMENTS

| | | | |
|---|---|---|---|
| 3,337,425 A | 8/1967 | Binning et al. | |
| 3,843,488 A | 10/1974 | Schmidt et al. | |
| 4,070,253 A | 1/1978 | Hofen et al. | |
| 6,395,913 B1 | 5/2002 | Barnicki et al. | |
| 6,500,970 B1 | 12/2002 | Barnicki et al. | |
| 6,582,565 B1 | 6/2003 | Barnicki et al. | |
| 7,138,534 B2 | 11/2006 | Forlin et al. | |
| 7,501,549 B2 | 3/2009 | Podrebarac et al. | |
| 8,766,028 B2 | 6/2014 | Wu et al. | |
| 10,053,401 B1 | 8/2018 | Beadle et al. | |
| 10,093,873 B2 | 10/2018 | Koseoglu et al. | |
| 10,131,592 B2 | 11/2018 | Lishchiner et al. | |
| 2017/0145317 A1 | 5/2017 | Lischiner et al. | |

FOREIGN PATENT DOCUMENTS

| | | |
|---|---|---|
| CN | 108912071 A | 11/2018 |
| EP | 0410689 A1 | 1/1991 |
| GB | 786301 A | 11/1957 |
| GB | 835770 A | 5/1960 |

OTHER PUBLICATIONS

U.S. Appl. No. 16/592,591, "Two Stage Hydrodearylation Systems and Processes to Convert Heavy Aromatics Into Gasoline Blending Components and Chemical Grade Aromatics", filed Oct. 10, 2019, (SA51330).

*Primary Examiner* — Sikarl A Witherspoon
(74) *Attorney, Agent, or Firm* — Bracewell LLP; Constance G. Rhebergen; Kevin R. Tamm (57) ABSTRACT

Systems and methods for reducing olefin concentration in a hydrocarbon stream comprising aromatic compounds and olefins, the method including supplying an aromatic-rich olefinic hydrocarbon stream; combining the aromatic-rich olefinic hydrocarbon stream with a catalyst; heating the aromatic-rich olefinic hydrocarbon stream and the catalyst to effect a reaction selected from the group consisting of: oxidation of olefins; hydration of olefins; and combinations of the same; separating an aqueous phase from a produced hydrocarbon phase; and separating $C_7$ compounds from $C_{8+}$ compounds in the produced hydrocarbon phase.

41 Claims, 5 Drawing Sheets

SYSTEMS AND PROCESSES TO DEOLEFINATE AROMATIC-RICH HYDROCARBON STREAMS

BACKGROUND

Field

Embodiments of the disclosure relate to systems and processes for upgrading products of an aromatics recovery complex. In particular, certain embodiments of the disclosure relate to systems and processes for oxidation in addition to or alternative to hydration of olefins to produce oxygen-containing hydrocarbons, optionally for use as gasoline blending components.

Description of the Related Art

Benzene, toluene, and xylenes (BTX) are mainly produced by the catalytic reforming of naphtha and pyrolysis gasoline (Pygas). Among these aromatic compounds, para-xylene (PX) is an important molecule and is used as a building block in the production of polyethylene terephthalate (PET). PET is used in the production of plastic bottles and a variety of synthetic fibers.

BTX are recovered in an aromatic recovery complex (ARC), which includes a combination of process units including olefin separation, para-xylene separation, xylene isomerization, toluene and heavy aromatic conversion, toluene selective disproportionation, trans-alkylation and aromatics extraction units. Olefinic and/or di-olefinic hydrocarbon impurities are commonly found in aromatic hydrocarbon process streams. Removal of olefins is important for meeting product specification requirements and for preventing process complications in downstream operations.

One common practice for removing olefins in an ARC is the use of a traditional clay treating process. Heavy hydrocarbons formed in clay towers are disposed in an ARC bottoms stream, and this results in a surplus waste stream for a given refinery. Olefins in addition to or alternative to di-olefins can also be removed by selective hydrogenation. Both processes have certain advantages and disadvantages, and current technologies exhibit multiple deficiencies in removing olefins from aromatic-rich streams.

In a typical ARC, an aromatic-rich stream from a reforming unit is split into two fractions: a $C_5$-$C_6$ fraction and $C_7^+$ fraction. The first fraction containing benzene and light hydrocarbons is recovered in a benzene extraction unit. A $C_7$ fraction is separated from a $C_{8+}$ fraction, and the $C_{8+}$ fraction is first de-olefinated before xylenes are separated. Olefins and di-olefins in minor amounts that form in the reforming process are undesirable in an ARC, as they cause process difficulties downstream of the unit. Therefore, the $C_{8+}$ fraction is de-olefinated before xylenes recovery.

Non-aromatic compounds are removed either in an extractive distillation unit or in a liquid-liquid extraction process. The latter is preferred when substantially pure toluene production is envisaged or when an external feed, such as hydrotreated Pygas, is to go through BTX extraction. Extractive distillation is ideally used when toluene is internally trans-alkylated. De-heptanizer bottoms are sent to a xylene rerun column, together with effluent from a trans-alkylation unit and recycle from an isomerization unit. The $C_8$ fraction, taken overhead from a xylene rerun column, feeds a xylene separation unit, which produces high purity para-xylene from the mixed $C_8$ stream at high recovery rates. A para-xylene-depleted stream then feeds the isomerization unit, which includes ethylbenzene reforming or de-alkylation technologies. Effluent from an isomerization process, a close-to-equilibrium mixture of xylenes, is then recycled to the xylene rerun and xylene separation units.

Xylene rerun column bottoms are sent to a heavy aromatics column where $C_9$ and $C_{10}$ aromatics are taken overhead as a trans-alkylation feed. The trans-alkylation step increases para-xylene production by disproportionation and trans-alkylation of toluene and $C_9^+$ aromatics, yielding additional mixed xylenes and benzene.

Olefinic hydrocarbon impurities are commonly found in aromatic hydrocarbon process streams. Removal of these olefins is important to meet product specification or purity standards required by aromatic producers. If olefins are not removed, they will react with other compounds to produce undesirable co-products, such as colored materials in benzene sulfonates. Olefins are also detrimental process poisons in downstream petrochemical processes, which are particularly sensitive to olefins even at parts per million concentrations. Olefins will also interact in downstream adsorption processes, thereby adversely affecting separation performance. Olefins can cause equipment fouling in a xylene column reboiler at high temperatures.

In traditional clay treating processes, a hydrocarbon stream is contacted with a clay composed primarily of amorphous and crystalline mixtures of silica and alumina. However, the acidic nature of the clays causes olefins in an aromatic stream such as styrene to react with aromatics via an alkylation reaction to produce uncondensed diaryl compounds, which deteriorate the quality of aromatic bottom fractions. Olefins also can be removed by selective hydrogenation, but existing technologies are insufficient for removing olefins from aromatic-rich feeds.

SUMMARY

Applicant has recognized a need for olefin hydration and olefin oxidation systems and processes, particularly for removing olefins from aromatic-rich streams to produce gasoline blending components in association with aromatics recovery complexes.

In one embodiment, an aromatic-rich hydrocarbon stream containing olefins and di-olefins is oxidized and converted into corresponding oxides, thereby eliminating formation of diaryl compounds that form in conventional clay towers. Product oxides have greater boiling points (for example, about 65° C.) compared to corresponding olefins, and as a result will shift into a heavy distillation boiling point range fraction. Hydration in addition to or alternative to oxidation as described throughout the disclosure can replace the need for clay towers; however, in some other embodiments, hydration in addition to or alternative to oxidation units can be followed by clay towers, which can be used in series.

In another embodiment, olefins present in an aromatic-rich hydrocarbon stream are hydrated with water and converted into corresponding alcohols, thereby eliminating the formation of diaryl compounds that form in conventional clay towers. Product alcohols have greater boiling points (for example, about 75° C.) than corresponding olefins, and as a result will shift into a heavy distillation boiling point range fraction and proceed to the aromatic complex bottoms, $C_9^+$ fraction. The oxygen-containing hydrocarbons produced in both embodiments, which have greater octane numbers in a range of about 95 to about 105, will be used as gasoline blending components. Furthermore, epoxide products can be treated to form alcohols, esters, ethers or combinations thereof, which are all greater-octane-possessing gasoline blending components. For example, suitable reactions include hydration followed by solvolysis or nucleophilic substitution.

Conventional clay tower treatment methods produce a bottom fraction that deteriorates the gasoline fraction. Embodiments disclosed here eliminate or reduce the need for clay towers, and this in turn eliminates formation of uncondensed di-aromatics formed in clay towers, such as diphenyl methane.

Oxidation or hydration of olefins in aromatic-rich streams effectively produce octane-rich gasoline blending components. Certain embodiments disclosed here selectively oxidize olefins, particularly olefins attached to an aromatic ring such as styrene and its alkylate derivatives.

Therefore, disclosed is a method for reducing olefin concentration in a hydrocarbon stream comprising aromatic compounds and olefins, the method including supplying an aromatic-rich olefinic hydrocarbon stream; combining the aromatic-rich olefinic hydrocarbon stream with a catalyst; heating the aromatic-rich olefinic hydrocarbon stream and the catalyst to effect oxidation of olefins; separating an aqueous phase from a produced hydrocarbon phase; and separating $C_7$ compounds from $C_{8+}$ compounds in the produced hydrocarbon phase. In some embodiments, the catalyst includes a metal from Group IVB to Group VIIIB of the Periodic Table. In certain other embodiments of the method, the catalyst comprises a homogeneous catalyst in the aromatic-rich olefinic hydrocarbon stream. Still in other embodiments, the step of combining the aromatic-rich olefinic hydrocarbon stream with the catalyst further comprises adding an oxidant to the aromatic-rich olefinic hydrocarbon stream. In yet other embodiments, the oxidant comprises a liquid oxidant and the step of heating heats to between about 20° C. to about 100° C.

Still in other embodiments, the catalyst comprises a heterogeneous catalyst. In certain embodiments, the step of combining the aromatic-rich olefinic hydrocarbon stream with the catalyst further comprises adding a gas phase oxidant to the aromatic-rich olefinic hydrocarbon stream. In still yet other embodiments, the step of heating heats to between about 20° C. to about 600° C. In certain embodiments, the step of heating effects oxidation using at least one compound selected from the group consisting of: hydrogen peroxide; an organic peroxide; a peroxo acid; an oxide of nitrogen; oxygen; air; and combinations of the same. Still in other embodiments, the aromatic-rich olefinic hydrocarbon stream comprises a hydrocarbon stream from an aromatics recovery complex. In certain other embodiments, the aromatic-rich olefinic hydrocarbon stream comprises a cracked feedstock from at least one of a catalytic reforming unit, a steam cracking unit, a catalytic cracking unit, and a thermal cracking unit. In other embodiments, the aromatic-rich olefinic hydrocarbon stream comprises a hydrocarbon stream boiling in the range of about 36° C. to about 240° C.

In other embodiments, the aromatic-rich olefinic hydrocarbon stream comprises aromatics at between about 20 wt. % to about 40 wt. % and comprises olefins at between about 0.1 wt. % and about 5 wt. %. Still in other embodiments, the separating step comprises the use of a separation unit selected from the group consisting of: a stripper; a fractionator; a flashing unit; and combinations of the same. Still in other embodiments, the step of heating takes place in a reactor selected from the group consisting of: a fixed-bed reactor, an ebullated-bed reactor, a continuously-stirred tank reactor, a batch reactor, a slurry-bed reactor, a moving-bed reactor; and combinations of the same.

In certain embodiments of systems and methods disclosed here, both oxidation and hydration are simultaneously effected to de-olefinate aromatic-rich olefin containing feeds. Further disclosed here is a system for carrying out the oxidation methods, the system including an aromatics recovery complex; a reactor fluidly coupled to an aromatic-rich olefinic hydrocarbon stream of the aromatics recovery complex and selected from the group consisting of: a fixed-bed reactor, an ebullated-bed reactor, a continuously-stirred tank reactor, a batch reactor, a slurry-bed reactor, a moving-bed reactor; and combinations of the same; a product separator unit fluidly coupled to the reactor and operable to receive a product stream from the reactor and separate the product stream into an aqueous phase and a hydrocarbon phase; and a hydrocarbon separator unit operable to separate $C_7$ compounds from $C_{8+}$ compounds in the hydrocarbon phase and selected from the group consisting of: a stripper; a fractionator; a flashing unit; and combinations of the same.

In some embodiments of the system, the reactor comprises a fixed bed catalyst. In other embodiments, the reactor is operable to accept a homogeneous catalyst stream. In certain embodiments, the reactor is operable to accept at least one of a liquid oxidant stream or a gaseous oxidant stream.

Additionally disclosed is a method for reducing olefin concentration in a hydrocarbon stream comprising aromatic compounds and olefins, the method including supplying an aromatic-rich olefinic hydrocarbon stream; combining the aromatic-rich olefinic hydrocarbon stream with a catalyst; heating the aromatic-rich olefinic hydrocarbon stream and the catalyst to effect hydration of olefins; separating an aqueous phase from a produced hydrocarbon phase; and separating $C_7$ compounds from $C_{8+}$ compounds in the produced hydrocarbon phase. In some embodiments, the aromatic-rich olefinic hydrocarbon stream comprises a hydrocarbon stream from an aromatics recovery complex. In other embodiments, the aromatic-rich olefinic hydrocarbon stream comprises a cracked feedstock from at least one of a catalytic reforming unit, a steam cracking unit, a catalytic cracking unit, and a thermal cracking unit.

In other embodiments, the aromatic-rich olefinic hydrocarbon stream comprises a hydrocarbon stream boiling in the range of about 36° C. to about 240° C. Still in other embodiments, the aromatic-rich olefinic hydrocarbon stream comprises aromatics between about 20 wt. % to about 40 wt. % and comprises olefins at between about 0.1 wt. % and about 5 wt. %. Still in other embodiments, the separating step comprises the use of a separation unit selected from the group consisting of: a stripper; a fractionator; a flashing unit; and combinations of the same. In yet some other embodiments of hydration methods, the catalyst includes a metal from at least one of IUPAC groups 4-10, 13 or 14. Still in other embodiments, the catalyst includes particles in the particle size range from about 0.15 mm to about 6 mm. In yet other embodiments, the catalyst surface area is in a range from about 10 m²/g to about 1000 m²/g.

In certain embodiments, the catalyst pore diameter is between about 10 angstroms to about 500 angstroms. Still in yet other certain embodiments, the catalyst comprises a homogeneous catalyst in the aromatic-rich olefinic hydrocarbon stream. In some embodiments, the step of combining the aromatic-rich olefinic hydrocarbon stream with the catalyst further comprises adding water to the aromatic-rich olefinic hydrocarbon stream. Still in other embodiments of hydration, the weight ratio of water to the aromatic-rich olefinic hydrocarbon stream is in the range of about 1:1 to about 8:1. In certain embodiments, the step of heating heats to between about 25° C. to about 300° C. In other embodiments, the catalyst comprises a heterogeneous catalyst. Still in other embodiments, the method includes the step of recycling a portion of the aqueous phase to the step of combining the aromatic-rich olefinic hydrocarbon stream with a catalyst. In yet other embodiments, the step of heating takes place in a reactor selected from the group consisting of: a fixed-bed reactor, an ebullated-bed reactor, a continuously-stirred tank reactor, a batch reactor, a slurry-bed reactor, a moving-bed reactor; and combinations of the same.

Additionally disclosed are systems for carrying out the methods of hydration, a system including an aromatics recovery complex; a reactor fluidly coupled to an aromatic-rich olefinic hydrocarbon stream of the aromatics recovery complex and selected from the group consisting of: a fixed-bed reactor, an ebullated-bed reactor, a continuously-stirred tank reactor, a batch reactor, a slurry-bed reactor, a moving-bed reactor; and combinations of the same; a product separator unit fluidly coupled to the reactor and operable to receive a product stream from the reactor and separate the product stream into an aqueous phase and a hydrocarbon phase; and a hydrocarbon separator unit operable to separate $C_7$ compounds from $C_{8+}$ compounds in the hydrocarbon phase and selected from the group consisting of: a stripper; a fractionator; a flashing unit; and combinations of the same.

In some embodiments, the reactor comprises a fixed bed catalyst. Still in other embodiments, the reactor is operable to accept a homogeneous catalyst stream. In yet other embodiments, the system further includes a recycle stream for the aqueous phase between the product separator unit and the reactor. Still in other embodiments, the reactor is operable to accept a water stream.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

DETAILED DESCRIPTION

So that the manner in which the features and advantages of the embodiments of systems and methods for oxidation in addition to or alternative to hydration of olefins in an aromatics recovery complex, may be understood in more detail, a more particular description of the embodiments of the present disclosure briefly summarized previously may be had by reference to the embodiments thereof, which are illustrated in the appended drawings, which form a part of this specification. It is to be noted, however, that the drawings illustrate only various embodiments of the disclosure and are therefore not to be considered limiting of the present disclosure's scope, as it may include other effective embodiments as well.

Figure 1:
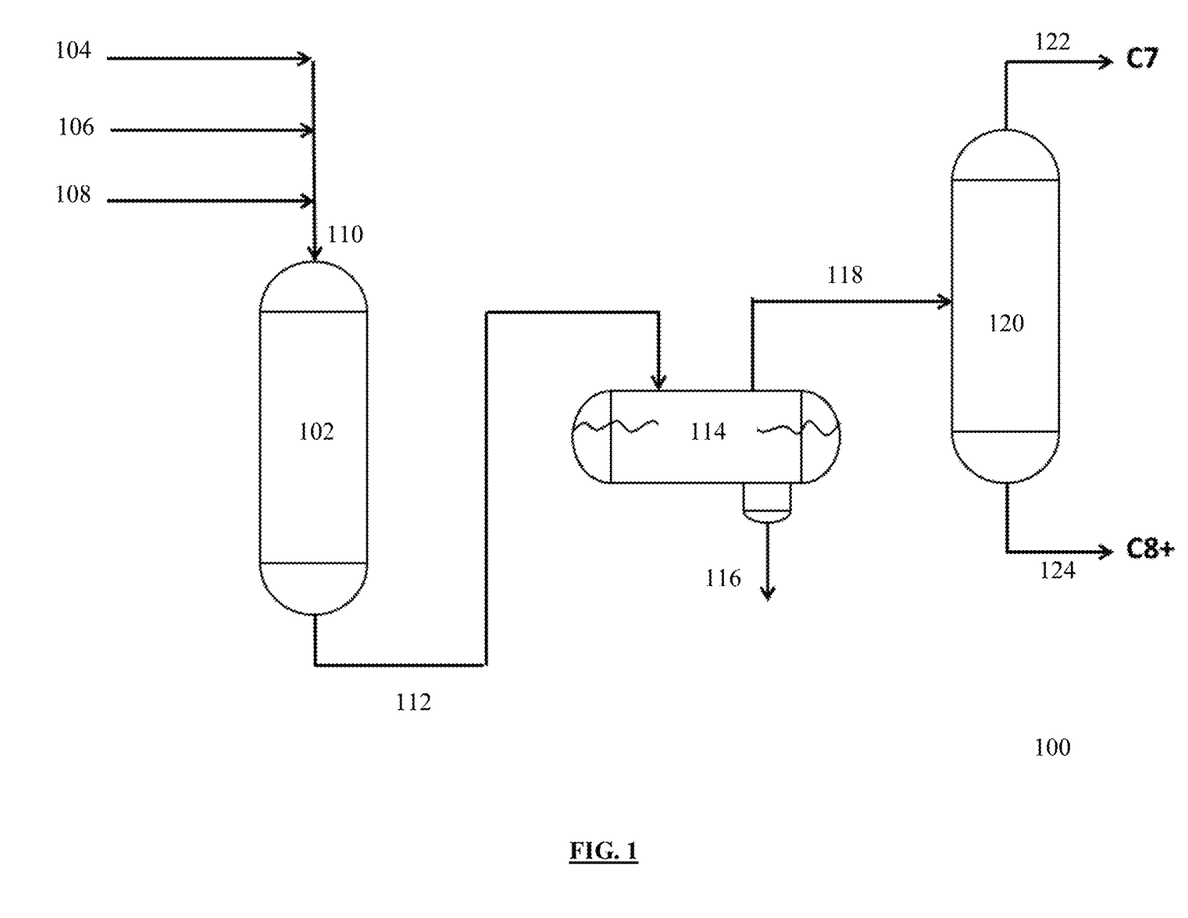
FIG. 1 is a schematic of a system and process for oxidation of a hydrocarbon feedstock comprising olefins using a homogeneous catalyst.

FIG. 1 is a schematic of a system and process for oxidation of a hydrocarbon feedstock comprising olefins using a homogeneous catalyst. FIG. 1 illustrates a liquid phase oxidation process with a homogeneous catalyst and a liquid phase oxidant. Oxidation system 100 includes a two-phase oxidation reactor 102 which operates using a hydrocarbon liquid phase and aqueous liquid phase. Aromatic-rich olefinic stream 104, oxidant stream 106, and homogeneous catalyst stream 108 are fed to two-phase oxidation reactor 102 via mixed stream 110. A de-olefinated aromatic-rich stream 112 produced by two-phase oxidation reactor 102 proceeds to a gas-liquid separator 114. An aqueous phase is withdrawn via stream 116 (with water and some mixed liquid hydrocarbons), and a mixed hydrocarbon phase comprising vapor and some liquids proceeds via line 118 to hydrocarbon separator 120. Hydrocarbon separator 120 includes in some embodiments any one of or any combination of a stripper, fractionator, or flashing unit. Hydrocarbon separator 120 produces a top stream 122 comprising $C_7$ hydrocarbons and a bottoms stream 124 comprising $C_{8+}$ hydrocarbons.

Figure 2:
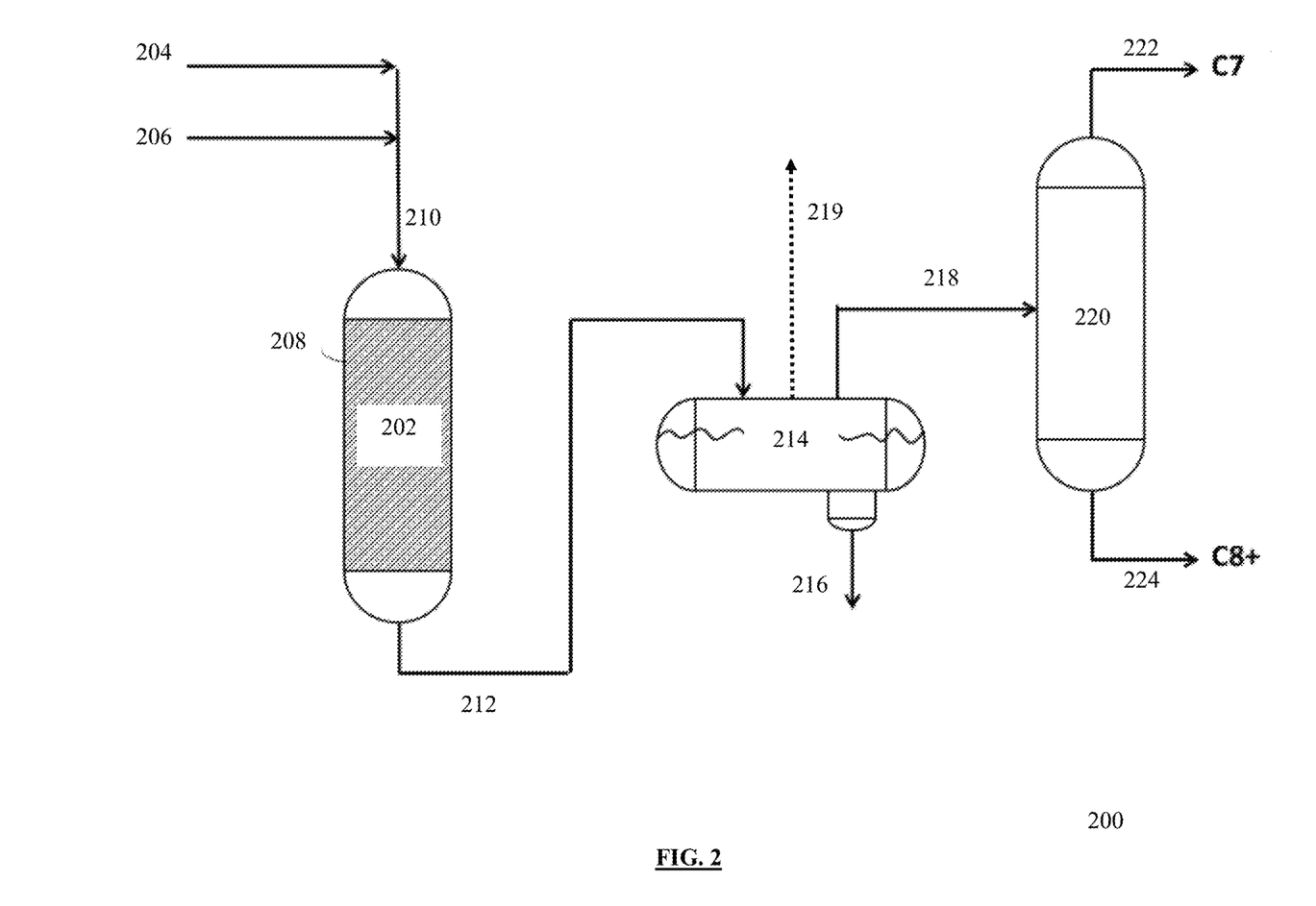
FIG. 2 is a schematic of a system and process for oxidation of a hydrocarbon feedstock comprising olefins using a heterogeneous catalyst.

FIG. 2 is a schematic of a system and process for oxidation of a hydrocarbon feedstock comprising olefins using a heterogeneous catalyst. FIG. 2 illustrates a gas phase oxidation using a heterogeneous catalyst packed in a reactor along with a gas phase oxidant. Oxidation system 200 includes a three-phase oxidation reactor 202 which operates using hydrocarbons in liquid phase, oxidant in a gas phase, and catalyst in a solid phase. Aromatic-rich olefinic stream 204 and oxidant stream 206 are fed to three-phase oxidation reactor 202 via mixed stream 210. Mixed stream 210 enters three-phase oxidation reactor 202 and contacts solid catalyst 208. A de-olefinated aromatic-rich stream 212 produced by three-phase oxidation reactor 202 proceeds to a gas-liquid separator 214. An aqueous phase is withdrawn via stream 216 (with water and some liquid hydrocarbons), and a mixed hydrocarbon phase comprising vapor and some liquids comprising oxidized hydrocarbons proceeds via line 218 to hydrocarbon separator 220. Hydrocarbon separator 220 includes in some embodiments any one of or any combination of a stripper, fractionator, or flashing unit. Hydrocarbon separator 220 produces a top stream 222 comprising $C_7$ hydrocarbons and a bottoms stream 224 comprising $C_{8+}$ hydrocarbons.

In some embodiments of FIG. 2, separator 214 includes a vertical separation column (not pictured), and separator 214 operates to produce three separate products, including an optional top stream 219 comprising unreacted gaseous oxidant. A separate mixed hydrocarbon phase comprising vapor and liquids comprising oxidized hydrocarbons proceeds via line 218 to hydrocarbon separator 220. An aqueous phase is withdrawn via stream 216 (with water and some liquid hydrocarbons). Hydrocarbon separator 220 includes in some embodiments any one of or any combination of a stripper, fractionator, or flashing unit. Hydrocarbon separator 220 produces a top stream 222 comprising $C_7$ hydrocarbons and a bottoms stream 224 comprising $C_{8+}$ hydrocarbons.

In the embodiments of FIGS. 1 and 2, suitable oxidants can include any one of or any combination of hydrogen peroxide, organic peroxides such as tert-butyl hydroperoxide, peroxo acids, oxides of nitrogen, oxygen, and air. Suitable oxidants to be applied as a liquid include hydrogen peroxide, organic peroxides such as tert-butyl hydroperoxide, and peroxo acids. Suitable gaseous oxidants include oxides of nitrogen, oxygen, and air. While the embodiments of FIGS. 1 and 2 show separate application of liquid oxidant with homogeneous catalyst and gaseous oxidant with heterogeneous catalyst, in other embodiments combinations of liquid and gas oxidants with combinations of homogeneous and heterogeneous catalysts can be applied for suitable de-olefination via oxidation.

In the embodiments of FIGS. 1 and 2, homogeneous and heterogeneous oxidation catalysts include metals from Group IVB to Group VIIIB of the periodic table. Homogeneous oil-soluble catalysts include one or more active metal components of metals or metal compounds (oxides, sulfides, or salts of organo-metal complexes) selected from the Periodic Table of the Elements IUPAC Groups 4, 5, 6, 7, 8, 9 and 10. In certain embodiments, homogeneous catalysts are transition-metal-based compounds derived from an organic acid salt or an organo-metal compound containing molybdenum, vanadium, tungsten, chromium, iron, or combinations of the same. In certain embodiments homogeneous catalysts can be selected from the group consisting of vanadium pentoxide, molybdenum alicyclic and aliphatic carboxylic acids, molybdenum naphthenate, nickel 2-ethylhexanoate, iron pentacarbonyl, molybdenum 2-ethyl hexanoate, molybdenum di-thiocarboxylate, nickel naphthenate, iron naphthenate, and combinations of the same.

In the embodiment of FIG. 1 applying liquid oxidants, feed temperatures and the temperature of two-phase oxidation reactor 102 can range between about 20° C. to about 100° C. In the embodiment of FIG. 2 applying gaseous oxidants, feed temperatures and the temperature of three-phase oxidation reactor 202 can range between about 20° C. to about 600° C. In the embodiment of FIG. 1 applying liquid oxidants, feed pressures and the pressure of two-phase oxidation reactor 102 can range between about 1 bar to about 30 bars. In the embodiment of FIG. 2 applying gaseous oxidants, feed pressures and the pressure of three-phase oxidation reactor 202 can range between about 20 bars to about 100 bars. For reactors 102, 202, the oxidant to olefin mole ratio can be between about 2 and about 6, for example about 4. For reactors 102, 202, the catalyst to feed mole ratio can be between about 0.01 and about 4. For reactors 102, 202, the residence time can be between about 1 minute and about 120 minutes, or between about 15 minutes and about 60 minutes.

For separation units 114, 214, 120, 220, temperature and pressure is designed to be less than the reactor due to pressure and heat losses, and residence time in a suitable separator vessel can be between about 10 minutes and about 30 minutes, for example about 15 minutes. In some example embodiments, hydrogen peroxide is applied as an oxidant at about 33 wt. % in solution.

Suitable feedstocks in FIGS. 1 and 2 for aromatic-rich olefinic streams 104 and 204, respectively, include olefin-containing hydrocarbon streams boiling in the range of about 36° C. to about 240° C., specifically cracked feedstock from catalytic reforming units, steam cracking units, catalytic cracking units, and thermal cracking units such as delayed coking units, fluid coking units, visbreaking units, and conventional thermal cracking units. In some embodiments, including FIGS. 1-4, aromatic-rich olefinic streams include at least about 70 wt. % aromatics, or at least about 80 wt. % aromatics. In some embodiments, including FIGS. 1-4, aromatic-rich olefinic streams include between about 1 wt. % and about 5 wt. % olefinics, or less than about 1 wt. % olefinics.

Suitable reactors in FIGS. 1 and 2 for two-phase oxidation reactor 102 and three-phase oxidation reactor 202, respectively, include fixed-bed reactors, ebullated-bed reactors, continuously-stirred tank reactors, batch reactors, slurry-bed reactors, and moving-bed reactors. For example, slurry batch and batch reactors, including continuously stirred tank reactors, are suitable for the embodiments of FIGS. 1 and 3, while fixed-bed reactors would be suitable for FIGS. 2 and 4.

Figure 3:
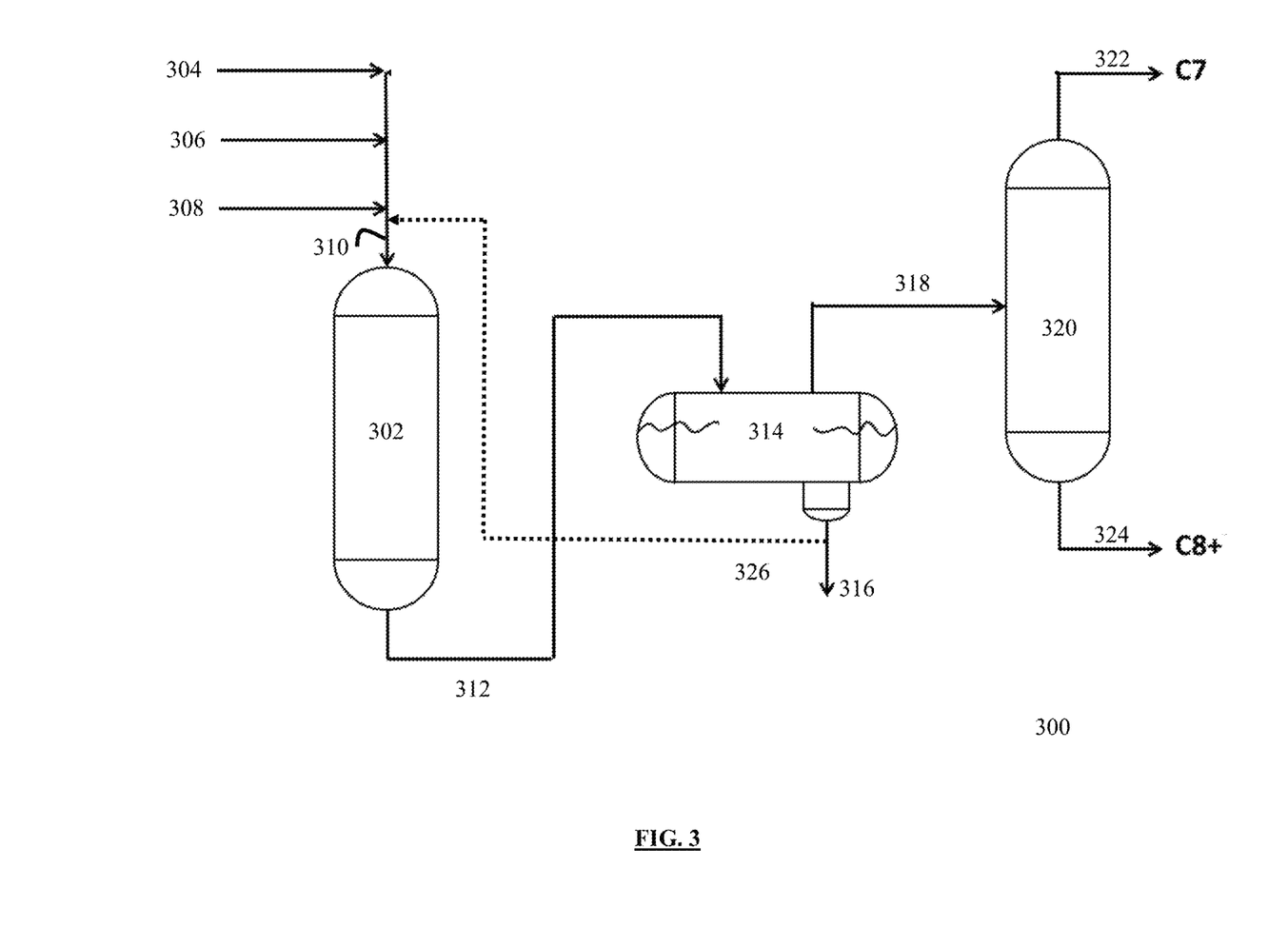
FIG. 3 is a schematic of a system and process for hydration of a hydrocarbon feedstock comprising olefins using a homogeneous catalyst.

FIG. 3 is a schematic of a system and process for hydration of a hydrocarbon feedstock comprising olefins using a homogeneous catalyst. FIG. 3 illustrates a two-phase hydration process using homogeneous catalyst along with hydrocarbons (oil phase) and water (aqueous phase). Hydration system 300 includes a two-phase hydration reactor 302 which operates using a hydrocarbon liquid phase and aqueous liquid phase. Aromatic-rich olefinic stream 304, water stream 306, and homogeneous catalyst stream 308 are fed to two-phase hydration reactor 302 via mixed stream 310. A de-olefinated aromatic-rich stream 312 produced by two-phase hydration reactor 302 proceeds to a gas-liquid separator 314. An aqueous phase is withdrawn via stream 316 (with water and produced soluble alcohols), and a mixed hydrocarbon phase with gas and liquid proceeds via stream 318 to hydrocarbon separator 320.

In one embodiment, for example, olefins in an aromatic-rich olefinic feed such as stream 304 include styrene, and a produced organic alcohol, for example in stream 312, includes phenethyl alcohol, which is slightly soluble in water at about 2 V %. Therefore, some of the soluble alcohol will leave the system with stream 316, and the remainder will be present in stream 318. Styrenes have low solubility in water. In certain embodiments, stream 326 can be optionally supplied back to two-phase hydration 302 as a recycle water supply and for recycle of some un-oxidized styrenes. Stream 316 can be bled from the system, depending on the need for recycle water and styrene.

Hydrocarbon separator 320 includes in some embodiments any one of or any combination of a stripper, fractionator, or flashing unit. Hydrocarbon separator 320 produces a top stream 322 comprising $C_7$ hydrocarbons and a bottoms stream 324 comprising $C_{8+}$ hydrocarbons and alcohols. In some embodiments, an amount of water added is about 35 times the styrene concentration in the feedstock. For example if styrenes are present at 1 wt. % of an aromatic-rich olefinic feed of 100 kg, the water added will be 35 kg. Styrene solubility in water is about 0.03 g/100 g and phenethyl alcohol solubility is about 0.02 g/100 g.

Figure 4:
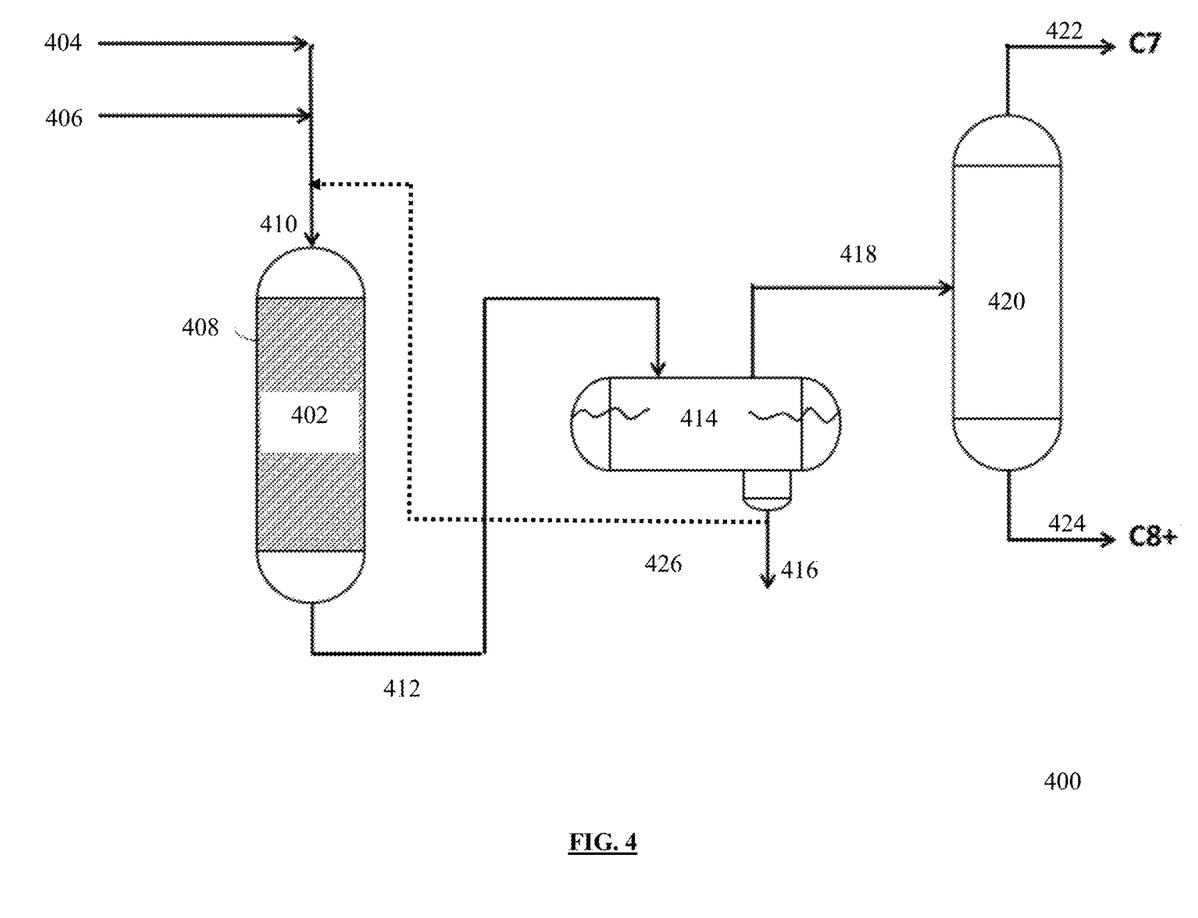
FIG. 4 is a schematic of a system and process for hydration of a hydrocarbon feedstock comprising olefins using a heterogeneous catalyst.

FIG. 4 is a schematic of a system and process for hydration of a hydrocarbon feedstock comprising olefins using a heterogeneous catalyst. FIG. 4 illustrates a three-phase hydration process using heterogeneous catalysts packed in a reactor. Hydration system 400 includes a three-phase hydration reactor 402 which operates using hydrocarbons in liquid phase, water in a liquid phase, and catalyst in a solid phase. Aromatic-rich olefinic stream 404 and water stream 406 are fed to three-phase hydration reactor 402 via mixed stream 410. Mixed stream 410 enters three-phase hydration reactor 402 and contacts solid catalyst 408.

A de-olefinated aromatic-rich stream 412 produced by three-phase hydration reactor 402 proceeds to a gas-liquid separator 414. An aqueous phase is withdrawn via stream 416 (with water and some produced soluble alcohols), and a hydrocarbon phase of mixed liquid and gas proceeds via line 418 to hydrocarbon separator 420. In one embodiment, for example, olefins in an aromatic-rich olefinic feed such as stream 404 include styrene, and a produced organic alcohol, for example in stream 412, includes phenethyl alcohol, which is slightly soluble in water at about 2 V %. Therefore, some of the soluble alcohol will leave the system with stream 416, and the remainder will be present in stream 418. Styrenes have low solubility in water. In certain embodiments, stream 426 can be optionally supplied back to two-phase hydration 402 as a recycle water supply and for recycle of some un-oxidized styrenes. Stream 416 can be bled from the system, depending on the need for recycle water and styrene.

Hydrocarbon separator 420 includes in some embodiments any one of or any combination of a stripper, fractionator, or flashing unit. Hydrocarbon separator 420 produces a top stream 422 comprising $C_7$ hydrocarbons and a bottoms stream 424 comprising $C_{8+}$ hydrocarbons and alcohols. In some embodiments, an amount of water added is about 35 times the styrene concentration in the feedstock. For example if styrenes are present at 1 wt. % of an aromatic-rich olefinic feed of 100 kg, the water added will 35 kg. Styrene solubility in water is about 0.03 g/100 g and phenethyl alcohol solubility is about 0.02 g/100 g.

Catalyst volume is determined in part by liquid hourly space velocity (LHSV), and a suitable range in the present disclosure for reactors 302, 402 is in the range of about 0.5 $h^{-1}$ to about 5 $h^{-1}$, or from about 1 $h^{-1}$ to about 2 $h^{-1}$. The conditions in separators 314 and 414 will be depend in part on the vessels, and suitable temperatures are in the range of about 180° C. to about 240° C. and pressure can be between about 20 bars to about 60 bars. A suitable residence time in the separation vessels is between about 5 and about 30 minutes, for example about 15 minutes. The same applies for separators 320, 420 for temperature, but suitable pressures will be less than about 3 bars.

In the embodiments of FIGS. 3 and 4, suitable feed pressures to and pressures within two-phase hydration reactor 302 and three-phase hydration reactor 402 can be between about 10 kg/cm² to about 120 kg/cm², between about 30 kg/cm² to about 80 kg/cm², and preferably between about 30 kg/cm² to about 50 kg/cm². While the embodiments of FIGS. 3 and 4 show separate application of liquid water with homogeneous catalyst and liquid water with heterogeneous catalyst, in other embodiments combinations of liquid water with combinations of homogeneous and heterogeneous catalysts can be applied for suitable de-olefination.

In the embodiments of FIGS. 3 and 4, suitable feed temperatures to and temperatures within hydration reactors 302, 402 can be between about 25° C. to about 300° C., between about 100° C. to about 250° C., and preferably from about 80° C. to about 200° C.

In the embodiments of FIGS. 3 and 4, catalysts can be selected from ion-exchange resins in addition to or alternative to amorphous or structured metal oxides. Suitable metals include those from IUPAC groups 4-10, 13 and 14. A suitable catalyst particle size is in the range of from about 0.15 mm to about 6 mm. A suitable surface area of the catalyst is in the range of from about 10 m²/g to about 1000 m²/g, or in the range from about 20 m²/g to about 500 m²/g, and preferably in the range from about 30 m²/g to about 100 m²/g. Pore diameter of the catalyst is in the range of from about 10 angstroms to about 500 angstroms, or from about 100 angstroms to about 400 angstroms, and preferably from about 200 angstroms to about 300 angstroms. The catalysts generally possess Bronsted acidity. Homogeneous catalysts for hydration include sulfuric acid and phosphoric acid. Heterogeneous catalysts for hydration include any acidic material including resins, and zeolites such as mordenite, beta, ZSM-5, and Faujasite.

In the embodiments of FIGS. 3 and 4, a suitable weight ratio of recycled hydration zone reaction products in streams 326, 426, respectively, to fresh olefinic feedstock from streams 304, 404, respectively, can be about 1:30, about 1:10, and preferably about 1:5. Liquid hourly space velocity of the olefinic feedstock is between about 0.1 to about 10.0 volume of feed per hour per volume of reactor ($h^{-1}$), or from about 0.5 to about 5.0 $h^{-1}$, and preferably from 1 to 2.0 $h^{-1}$.

In the embodiments of FIGS. 3 and 4, a suitable water to olefin weight ratio is in the range of about 1:1 to about 8:1, or about 1:1 to about 35:1.

Embodiments of systems and methods disclosed here optimize aromatic complex de-olefinating of aromatic-rich streams, and as a result heavy aromatic bottoms formation is reduced or eliminated, and octane-rich gasoline streams are produced.

Figure 5:
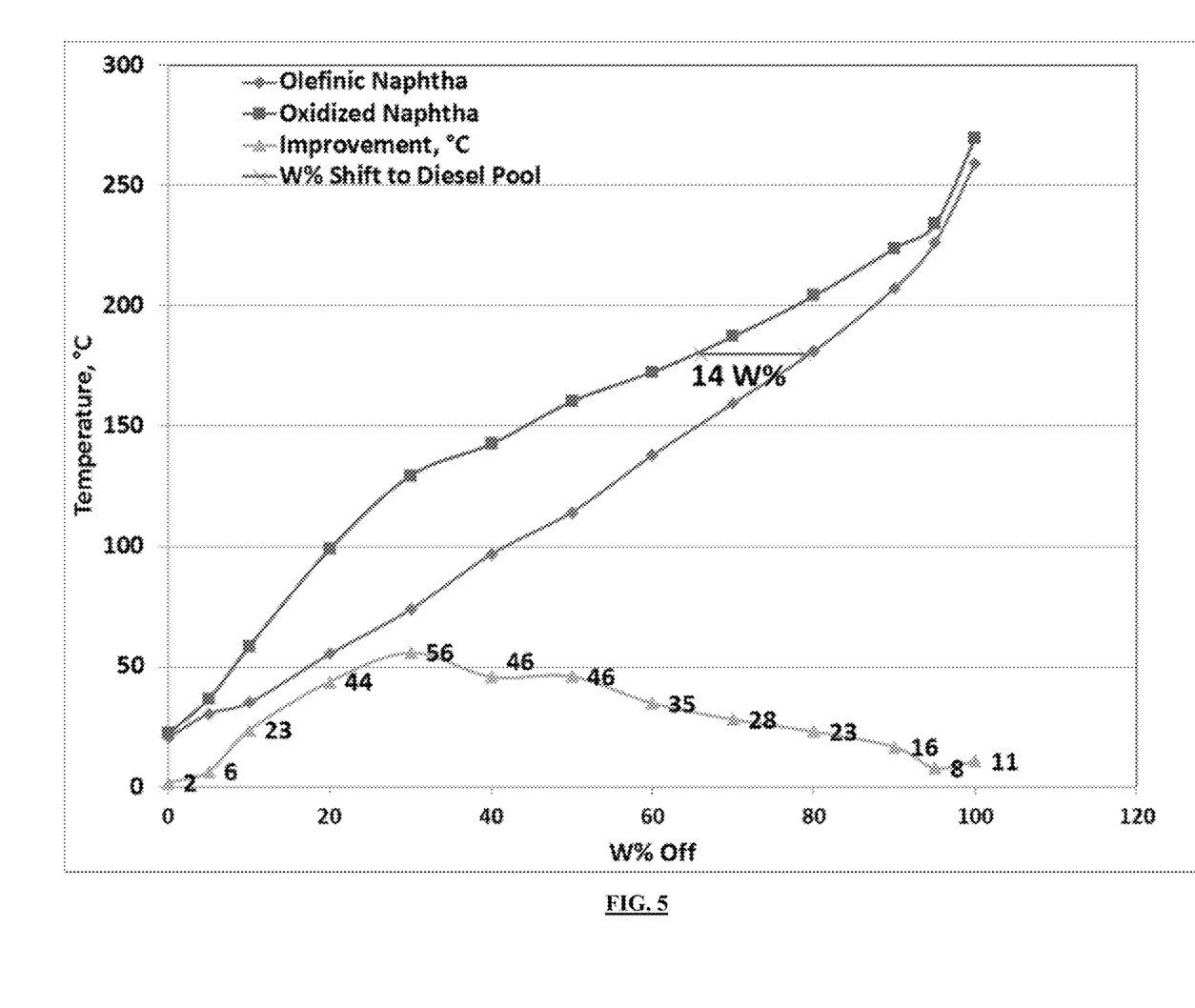
FIG. 5 is a graph showing the results of Example 1 including distillation curves for feedstock and oxidized products.

Example 1: Oxidation 20 g of aromatic-rich olefin-containing naphtha was oxidized in a vessel containing 0.3 g of sodium tungstate ($Na_2WO_4.2H_2O$), 1.3 grams of acetic acid, and 24 grams of hydrogen peroxide. The mixture was refluxed at 80° C. for 60 minutes. The mixture was cooled, and the hydrocarbon phase was separated from the aqueous phase. The feedstock and product were also analyzed by simulated distillation (ASTM D2887). FIG. 5 shows a shift in boiling point. 14 wt. % of the fraction shifted to diesel boiling material, indicative of oxide formation.

Example 2: Hydration 50 cc of aromatic-rich olefin containing naphtha was added to a one-liter round bottom flask and cooled in an ice bath for about three minutes. 50 cc of 75% (v/v) sulfuric acid was then slowly added to the cooled naphtha while stirring the mixture with a glass rod. After all of the acid was added, the mixture was stirred until a single homogeneous layer formed. The mixture was allowed to stand in the ice bath for another 5 minutes, after which 50 cc of cold water was added. The mixture separated into two layers, the upper layer containing the hydrated naphtha, and the lower layer containing mainly the aqueous sulfuric acid. The naphtha feedstock and the treated product were analyzed using the paraffins, isoparaffins, olefins, naphthenes, aromatics (PIONA) method, the results of which are tabulated in Table 1. The PIONA method analyzes fractions boiling up to 180° C. As seen in this range of naphtha, 23.8 wt. % of olefins are converted. An increase in aromatics and naphthenes is also shown by the PIONA analysis.

TABLE 1

Feedstock Properties and Results for Example 2.

|  | Feedstock Naphtha (Wt. %) | Treated Naphtha (Wt. %) |
|---|---|---|
| Paraffins | 28.5 | 28.6 |
| Aromatics | 31.7 | 38.7 |
| Olefins | 33.7 | 25.2 |
| Naphthenes | 5.9 | 7.3 |
| Unidentified | 0.2 | 0.1 |
| Total | 100 | 100 |

In this example, naphtha was used to illustrate olefin hydration. Reformate does not exhibit, typically, such high levels of olefins, and therefore water requirements would be less than exemplified here.

The singular forms "a," "an," and "the" include plural referents, unless the context clearly dictates otherwise. The term "about" when used with respect to a value or range refers to values including plus and minus 5% of the given value or range.

One of ordinary skill in the art will understand that standard components such as pumps, compressors, temperature and pressure sensors, valves, and other components not shown in the drawings would be used in applications of the systems and methods of the present disclosure.

In the drawings and specification, there have been disclosed example embodiments of the present disclosure, and although specific terms are employed, the terms are used in a descriptive sense only and not for purposes of limitation. The embodiments of the present disclosure have been described in considerable detail with specific reference to these illustrated embodiments. It will be apparent, however, that various modifications and changes can be made within the spirit and scope of the disclosure as described in the foregoing specification, and such modifications and changes are to be considered equivalents and part of this disclosure.

That claimed is:

1. A method for reducing olefin concentration in a hydrocarbon stream comprising aromatic compounds and olefins, the method comprising the steps of:
    supplying an aromatic-rich olefinic hydrocarbon stream;
    combining the aromatic-rich olefinic hydrocarbon stream with a catalyst;
    heating the aromatic-rich olefinic hydrocarbon stream and the catalyst to effect oxidation of olefins;
    separating an aqueous phase from a produced hydrocarbon phase; and
    separating $C_7$ compounds from $C_{8+}$ compounds in the produced hydrocarbon phase.

2. The method according to claim 1, where the catalyst includes a metal from Group IVB to Group VIIIB of the Periodic Table.

3. The method according to claim 1, where the catalyst comprises a homogeneous catalyst in the aromatic-rich olefinic hydrocarbon stream.

4. The method according to claim 1, where the step of combining the aromatic-rich olefinic hydrocarbon stream with the catalyst further comprises adding an oxidant to the aromatic-rich olefinic hydrocarbon stream.

5. The method according to claim 4, where the oxidant comprises a liquid oxidant and the step of heating heats to between about 20° C. to about 100° C.

6. The method according to claim 1, where the catalyst comprises a heterogeneous catalyst.

7. The method according to claim 6, where the step of combining the aromatic-rich olefinic hydrocarbon stream with the catalyst further comprises adding a gas phase oxidant to the aromatic-rich olefinic hydrocarbon stream.

8. The method according to claim 7, where the step of heating heats to between about 20° C. to about 600° C.

9. The method according to claim 1, where the step of heating effects oxidation using at least one compound selected from the group consisting of: hydrogen peroxide; an organic peroxide; a peroxo acid; an oxide of nitrogen; oxygen; air; and combinations of the same.

10. The method according to claim 1, where the aromatic-rich olefinic hydrocarbon stream comprises a hydrocarbon stream preceding or from an aromatics recovery complex.

11. The method according to claim 1, where the aromatic-rich olefinic hydrocarbon stream comprises a cracked feedstock from at least one of a catalytic reforming unit, a steam cracking unit, a catalytic cracking unit, and a thermal cracking unit.

12. The method according to claim 1, where the aromatic-rich olefinic hydrocarbon stream comprises a hydrocarbon stream boiling in the range of about 36° C. to about 240° C.

13. The method according to claim 1, where the aromatic-rich olefinic hydrocarbon stream comprises aromatics at between about 20 wt. % to about 40 wt. % and comprises olefins at between about 0.1 wt. % and about 5 wt. %.

14. The method according to claim 1, where the separating step comprises the use of a separation unit selected from the group consisting of: a stripper; a fractionator; a flashing unit; and combinations of the same.

15. The method according to claim 1, where the step of heating takes place in a reactor selected from the group consisting of: a fixed-bed reactor, an ebullated-bed reactor, a continuously-stirred tank reactor, a batch reactor, a slurry-bed reactor, a moving-bed reactor; and combinations of the same.

16. A system for carrying out the method of claim 1, the system comprising:
    an aromatics recovery complex;
    a reactor fluidly coupled to an aromatic-rich olefinic hydrocarbon stream of the aromatics recovery complex and selected from the group consisting of: a fixed-bed reactor, an ebullated-bed reactor, a continuously-stirred tank reactor, a batch reactor, a slurry-bed reactor, a moving-bed reactor; and combinations of the same;
    a product separator unit fluidly coupled to the reactor and operable to receive a product stream from the reactor and separate the product stream into an aqueous phase and a hydrocarbon phase; and
    a hydrocarbon separator unit operable to separate $C_7$ compounds from $C_{8+}$ compounds in the hydrocarbon phase and selected from the group consisting of: a stripper; a fractionator;
    a flashing unit; and combinations of the same.

17. The system according to claim 16, where the reactor comprises a fixed bed catalyst.

18. The system according to claim 16, where the reactor is operable to accept a homogeneous catalyst stream.

19. The system according to claim 16, where the reactor is operable to accept at least one of a liquid oxidant stream or a gaseous oxidant stream.

20. A method for reducing olefin concentration in a hydrocarbon stream comprising aromatic compounds and olefins, the method comprising the steps of:
    supplying an aromatic-rich olefinic hydrocarbon stream;
    combining the aromatic-rich olefinic hydrocarbon stream with a catalyst;
    heating the aromatic-rich olefinic hydrocarbon stream and the catalyst to effect hydration of olefins;
    separating an aqueous phase from a produced hydrocarbon phase; and
    separating $C_7$ compounds from $C_{8+}$ compounds in the produced hydrocarbon phase.

21. The method according to claim 20, where the aromatic-rich olefinic hydrocarbon stream comprises a hydrocarbon stream preceding or from an aromatics recovery complex.

22. The method according to claim 20, where the aromatic-rich olefinic hydrocarbon stream comprises a cracked feedstock from at least one of a catalytic reforming unit, a steam cracking unit, a catalytic cracking unit, and a thermal cracking unit.

23. The method according to claim 20, where the aromatic-rich olefinic hydrocarbon stream comprises a hydrocarbon stream boiling in the range of about 36° C. to about 240° C.

24. The method according to claim 20, where the aromatic-rich olefinic hydrocarbon stream comprises aromatics between about 20 wt. % to about 40 wt. % and comprises olefins at between about 0.1 wt. % and about 5 wt. %.

25. The method according to claim 20, where the separating step comprises the use of a separation unit selected from the group consisting of: a stripper; a fractionator; a flashing unit; and combinations of the same.

26. The method according to claim 20, where the catalyst includes a metal from at least one of IUPAC groups 4-10, 13 or 14.

27. The method according to claim 20, where the catalyst includes particles in the particle size range from about 0.15 mm to about 6 mm.

28. The method according to claim 20, where the catalyst surface area is in a range from about 10 $m^2/g$ to about 1000 $m^2/g$.

29. The method according to claim 20, where the catalyst pore diameter is between about 10 angstroms to about 500 angstroms.

30. The method according to claim 20, where the catalyst comprises a homogeneous catalyst in the aromatic-rich olefinic hydrocarbon stream.

31. The method according to claim 20, where the step of combining the aromatic-rich olefinic hydrocarbon stream with the catalyst further comprises adding water to the aromatic-rich olefinic hydrocarbon stream.

32. The method according to claim 31, where the weight ratio of water to the aromatic-rich olefinic hydrocarbon stream is in the range of about 1:1 to about 8:1.

33. The method according to claim 20, where the step of heating heats to between about 25° C. to about 300° C.

34. The method according to claim 20, where the catalyst comprises a heterogeneous catalyst.

35. The method according to claim 20, further comprising the step of recycling a portion of the aqueous phase to the step of combining the aromatic-rich olefinic hydrocarbon stream with a catalyst.

36. The method according to claim 20, where the step of heating takes place in a reactor selected from the group consisting of: a fixed-bed reactor, an ebullated-bed reactor, a continuously-stirred tank reactor, a batch reactor, a slurry-bed reactor, a moving-bed reactor; and combinations of the same.

37. A system for carrying out the method of claim 20, the system comprising:
an aromatics recovery complex;
a reactor fluidly coupled to an aromatic-rich olefinic hydrocarbon stream of the aromatics recovery complex and selected from the group consisting of: a fixed-bed reactor, an ebullated-bed reactor, a continuously-stirred tank reactor, a batch reactor, a slurry-bed reactor, a moving-bed reactor; and combinations of the same;
a product separator unit fluidly coupled to the reactor and operable to receive a product stream from the reactor and separate the product stream into an aqueous phase and a hydrocarbon phase; and
a hydrocarbon separator unit operable to separate $C_7$ compounds from $C_{8+}$ compounds in the hydrocarbon phase and selected from the group consisting of: a stripper; a fractionator;
a flashing unit; and combinations of the same.

38. The system according to claim 37, where the reactor comprises a fixed bed catalyst.

39. The system according to claim 37, where the reactor is operable to accept a homogeneous catalyst stream.

40. The system according to claim 37, further comprising a recycle stream for the aqueous phase between the product separator unit and the reactor.

41. The system according to claim 37, where the reactor is operable to accept a water stream.

* * * * *